(12) United States Patent
Lin et al.

(10) Patent No.: US 7,196,215 B2
(45) Date of Patent: Mar. 27, 2007

(54) PROCESS FOR THE PRODUCTION OF PURIFIED TEREPHTHALIC ACID

(75) Inventors: Robert Lin, Kingsport, TN (US); Ruairi Seosamh O'Meadhra, Kingsport, TN (US); Ronald Buford Sheppard, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/161,571

(22) Filed: May 31, 2002

(65) Prior Publication Data

US 2002/0193630 A1 Dec. 19, 2002

Related U.S. Application Data

(60) Provisional application No. 60/295,619, filed on Jun. 4, 2001.

(51) Int. Cl.
*C07C 51/42* (2006.01)
*C07C 51/255* (2006.01)
*C07C 309/00* (2006.01)

(52) U.S. Cl. ............... 562/486; 562/485; 562/487; 562/417; 562/416; 562/77

(58) Field of Classification Search ........... 562/77, 562/486, 485, 487, 417, 416
See application file for complete search history.

(56) References Cited

U.S. PATENT DOCUMENTS

| | | | |
|---|---|---|---|
| 3,057,909 A | 10/1962 | Sebelist et al. | |
| 3,064,044 A | 11/1962 | Baldwin | |
| 3,452,088 A | 6/1969 | Olsen et al. | |
| 3,584,039 A * | 6/1971 | Meyer | 562/416 |
| 3,799,976 A * | 3/1974 | Nienburg et al. | 562/416 |
| 3,850,983 A | 11/1974 | Park | |
| 3,931,305 A | 1/1976 | Fisher | |
| 3,996,271 A | 12/1976 | Yokota et al. | |
| 4,158,738 A | 6/1979 | Scott et al. | |
| 4,356,319 A | 10/1982 | Roffia et al. | |
| 4,438,279 A * | 3/1984 | Packer et al. | 562/416 |
| 4,467,111 A * | 8/1984 | Puskas et al. | 562/487 |
| 4,500,732 A | 2/1985 | Petty-Weeks et al. | |

(Continued)

FOREIGN PATENT DOCUMENTS

DE 1925038 11/1970

(Continued)

OTHER PUBLICATIONS

Arun Pal Aneja and Viney Pal Aneja, "The Effect of Water and Air Contamination on Poly(Ethylene Terephthalate) Formation", Polymer Engineering Reviews, 1982, pp. 123-133, vol. 2, No. 2.

(Continued)

*Primary Examiner*—Taylor Victor Oh
(74) *Attorney, Agent, or Firm*—Steven A. Owen; Bernard J. Graves, Jr.

(57) ABSTRACT

Disclosed is a process for the production of terephthalic acid by a plurality of process steps including the catalyst oxidation of a dialkylbenzene compound, a second oxidation, a hydrogenation of the product of the second oxidation, and crystallization of the hydrogenation terephthalic acid using a plurality of series-connected crystallizers.

18 Claims, 2 Drawing Sheets

U.S. PATENT DOCUMENTS

| | | | |
|---|---|---|---|
| 4,772,748 A | | 9/1988 | Hashizume et al. |
| 4,892,970 A | | 1/1990 | Nowicki et al. |
| 4,939,297 A | | 7/1990 | Browder et al. |
| 5,095,146 A | | 3/1992 | Zeitlin et al. |
| 5,110,984 A | * | 5/1992 | Janulis ............... 562/487 |
| 5,175,355 A | * | 12/1992 | Streich et al. ......... 562/485 |
| 5,510,521 A | | 4/1996 | McGehee et al. |
| 5,567,842 A | | 10/1996 | Izumisawa et al. |
| 5,583,254 A | | 12/1996 | Turner et al. |
| 5,756,833 A | | 5/1998 | Rosen et al. |
| RE36,008 E | * | 12/1998 | Hindmarsh et al. ...... 562/414 |
| 6,297,348 B1 | | 10/2001 | Rodden et al. |
| 6,689,903 B2 | | 2/2004 | O'Meadhra et al. |
| 2002/0183546 A1 | | 12/2002 | Sheppard et al. |
| 2002/0193630 A1 | | 12/2002 | Lin et al. |

FOREIGN PATENT DOCUMENTS

| | | |
|---|---|---|
| GB | 983677 | 2/1965 |
| GB | 983677 A | 2/1965 |
| GB | 1152575 A | 5/1969 |
| GB | 1 358 520 | 7/1974 |
| GB | 1358520 A | 7/1974 |
| GB | 1454478 A | 11/1976 |
| JP | 2001-288139 A | 10/2001 |

OTHER PUBLICATIONS

Co-pending U.S. Appl. No. 10/156,312, filed May 28, 2002.
Co-pending U.S. Appl. No. 10/423,389, filed Apr. 25, 2003.
PCT Notification of Transmittal of the International Search Report or the Declaration dated Sep. 26, 2002 in a case relating to U. S. Patent No. 6 689 903.
Copending U.S. Appl. No. 11/254,406, filed Oct. 20, 2005.
Copending U.S. Appl. No. 10/156,312, filed May 28, 2002.
Copending U.S. Appl. No. 10/423,389, filed Apr. 25, 2003.
USPTO Office Action dated Oct. 17, 2005 for U.S. Appl. No. 10/156,312.
USPTO Office Action dated Aug. 23, 2005 for U.S. Appl. No. 10/156,312.
USPTO Office Action dated May 27, 2004 for U.S. Appl. No. 10/156,312.
USPTO Office Action dated Apr. 22, 2005 for U.S. Appl. No. 10/156,312.
USPTO Office Action dated Oct. 3, 2003 for U.S. Appl. No. 10/156,312.
USPTO Office Action dated Dec. 4, 2002 for U.S. Appl. No. 10/156,312.
USPTO Office Action dated Nov. 23, 2005 for U.S. Appl. No. 10/423,389.
USPTO Office Action dated Jul. 13, 2005 for U.S. Appl. No. 10/423,389.
USPTO Office Action dated Feb. 7, 2005 for U.S. Appl. No. 10/423,389.
USPTO Office Action dated Jun. 30, 2004 for U.S. Appl. No. 10/423,389.

\* cited by examiner

PROCESS FOR THE PRODUCTION OF PURIFIED TEREPHTHALIC ACID

CROSS REFERENCE TO RELATED APPLICATION

This application claims the benefit of U.S. Provisional Application Ser. No. 60/295,619 filed Jun. 4, 2001.

FIELD OF THE INVENTION

This invention pertains to a novel process for the production of purified terephthalic acid by a novel combination of steps beginning with the oxidation of a dialkyl benzene compound such as p-xylene. More specifically, this invention pertains to the production of purified terephthalic acid by an oxidation process wherein a dialkyl benzene compound first is oxidized to a terephthalic acid by means of a two-stage process utilizing certain conditions to obtain the terephthalic acid having improved purity and then the terephthalic acid is purified by hydrogenation and recovered by a novel crystallization method.

BACKGROUND OF THE INVENTION

Aromatic dicarboxylic acids such as terephthalic acid and isophthalic acid are of great commercial importance and are widely used for the production of various polyester polymers such as fiber-forming and molding grade polyesters. Terephthalic acid (TPA) is one of the basic building blocks in the production of linear polyester resins used in the manufacture of polyester films, packaging materials and bottles. TPA used in the manufacture of such polyesters resins must meet certain minimum purity requirements. The purified condition of terephthalic acid refers primarily to the absence of significant concentrations of 4-carboxybenzaldehyde (4-CBA) and p-toluic acid that are present in significant quantities in the crude commercially-available grades of terephthalic acid. Both CBA and toluic acid are partial oxidation products formed in the manufacture of TPA by the catalytic oxidation of p-xylene. The purified form also refers to the absence of color bodies that impart a characteristic yellow hue to the crude material. The color bodies are aromatic compounds having the structures of benzils, fluorenones, and/or anthraquinones. 4-CBA and p-toluic acid are particularly detrimental to the polymerization process as they act as chain terminators during the condensation reaction between terephthalic acid and ethylene glycol in the production of poly(ethylene terephthalate) (PET).

Crude terephthalic acid may be purified by hydrogenation. In a typical hydrogenation process, the crude terephthalic acid is dissolved in water at elevated temperature and pressure and hydrogenated to convert the 4-CBA to p-toluic acid. The hydrogenation also converts the color bodies to colorless compounds. One constraint in developing a process for isolating the purified terephthalic acid from the hydrogenated liquor solution is the level of the 4-CBA and p-toluic acid acceptable in the final product. For example, purified terephthalic acid (PTA) typically contains on a weight basis less than 150 parts per million (ppmw) p-toluic acid. Isolation techniques to produce purified terephthalic acid use a wide variety of solid-liquid separation methods including crystallization, centrifugation, filtration, and combinations thereof.

Crude terephthalic acid obtained from the initial oxidation of a dialkylbenzene compound, normally p-xylene, typically contains a total concentration of 4-CBA and p-toluic acid of about 150 to 1100 ppmw based on the weight of the solids present. Crude terephthalic acid also contains lesser amounts, e.g., in the 20–200 ppmw range, of the characteristically yellow compounds. These compounds are colored aromatic compounds having the structures of benzil, fluorenone, and/or anthraquinone, which result from coupling side reactions occurring during the oxidation of p-xylene. It is necessary to purify the crude terephthalic acid when using it as a starting material for producing polyester fiber, which requires a purified terephthalic acid (PTA) as a starting material.

Such a purification process typically involves combining the crude terephthalic acid solid separated from the oxidation process with water to form a slurry thereof, which is heated to dissolve the crude terephthalic acid and impurities in the water and provide an aqueous solution. This solution is then passed to a reduction step in which the solution is contacted with hydrogen in the presence of a heterogeneous catalyst, usually palladium on a carbon support, at an elevated temperature such as 200 to 375° C. for the purification of TPA. The hydrogenation step converts the various color bodies present in the crude terephthalic acid to colorless products. The 4-CBA impurity is converted to p-toluic acid.

Subsequent separation and isolation of the terephthalic acid product can be accomplished via a wide variety of solid-liquid separation methods. A staged equilibrium crystallization approach is one separation method. With such an approach, evaporation is controlled against back pressure regulation in multiple crystallizer stages to control the rate at which the post-hydrogenation stream is crystallized. For terephthalic acid, it is believed that shock cooling of the post-hydrogenation stream to temperatures below 165° C. promotes the co-precipitation (co-crystallization) of impurities, particularly p-toluic acid, which contaminates the PTA product.

U.S. Pat. No. 3,931,305 discloses that the primary factor determining the impurity concentration in the terephthalic acid product is the lowest temperature to which the post-hydrogenation stream is flashed. The impurity concentration is less a function of the rate at which the post-hydrogenation stream is cooled. To this end, it is recommended that the majority of the terephthalic acid be crystallized at a temperature higher than about 160 to 182° C., which is the threshold temperature at which p-toluic acid co-crystallization becomes critical. When the post-hydrogenated stream of terephthalic acid has a concentration from 500 to 6,000 ppmw p-toluic acid, it is suggested to perform post-crystallization filtration at a temperature between about 121 and 149° C. to obtain a p-toluic acid concentration of 150 ppmw or less in the PTA product. Other isolation techniques use efficient filtration, washing, and drying methods within the temperature range of 100 to 205° C. to mitigate precipitation of p-toluic acid.

BRIEF SUMMARY OF THE INVENTION

The present invention provides a process for the production of purified TPA beginning with the oxidation of p-xylene. The present invention provides a process for the production and recovery of crystalline terephthalic acid containing less than about 150 parts per million by weight (ppmw) p-toluic acid, based on the weight of the terephthalic acid, by the steps comprising:

(1) feeding (i) a dialkyl benzene compound, (ii) aqueous acetic acid reaction medium having oxidation catalyst components dissolved therein, and (iii) an oxygen-containing gas to a first pressurized oxidation zone wherein liquid-phase, exothermic oxidation of the dialkyl benzene compound occurs, wherein the temperature and pressure within the first pressurized oxidation reactor are maintained at about 150 to 180° C. and about 3.5 to 13 bar absolute—bara (about 50 to 189 pounds per square inch—psia);

(2) removing from the upper portion of the first reactor a vapor comprising vaporized aqueous, acetic acid reaction medium and oxygen-depleted gas comprising carbon dioxide, methane, inert components, and less than about 9 volume percent, based on the non-condensable components of the vapor, oxygen;

(3) removing from the lower portion of the first reactor an oxidizer product comprising (i) solid and dissolved terephthalic acid and incomplete oxidation products and (ii) the aqueous, acetic acid reaction medium having the oxidation catalyst dissolved therein;

(4) feeding (i) the oxidizer product of step (3) and (ii) an oxygen-containing gas to a second pressurized oxidation zone wherein liquid-phase, exothermic oxidation of the incomplete oxidation products occurs, wherein the temperature and pressure within the second pressurized oxidation reactor are maintained at about 185 to 230° C. and about 4.5 to 18.3 bara (about 65 to 265 psia);

(5) removing from the upper portion of the second reactor a vapor comprising vaporized aqueous, acetic acid reaction medium and oxygen-depleted gas comprising carbon dioxide, methane, inert components, and less than about 5 volume percent, based on the non-condensable components of the vapor, oxygen;

(6) removing from the lower portion of the second reactor a second oxidizer product comprising (i) solid and dissolved terephthalic acid and (ii) the aqueous, acetic acid reaction medium having the oxidation catalyst dissolved therein;

(7) separating terephthalic acid from the (ii) the aqueous, acetic acid reaction medium of step (6) to obtain terephthalic acid containing 4-carboxybenzaldehyde and p-toluic acid impurities in a total concentration of about 400 to 900 ppmw;

(8) dissolving the terephthalic acid obtained in step (7) in water to form a solution containing about 10 to 35 weight percent dissolved terephthalic acid, at a temperature of about 260 to 320° C. and a pressure sufficient to maintain the solution in the liquid phase and contacting the solution with hydrogen in the presence of a hydrogenation catalyst to produce a hydrogenation product solution;

(9) feeding the solution of step (8) to a crystallization zone comprising a plurality of series-connected crystallizers wherein the solution is subjected to rate-controlled evaporative cooling by sequential reduction in pressure and temperature to cause crystallization of terephthalic acid, wherein the pressure of the solution at the end of the crystallization zone is about ambient pressure or less;

(10) condensing solvent evaporated from the crystallizers and returning the condensed solvent to the crystallization zone at a point subsequent to the crystallizer from which it was obtained; and

(11) recovering solid, crystalline terephthalic acid containing less than about 150 parts ppmw p-toluic acid, based on the weight of the terephthalic acid, by solid-liquid separation at ambient pressure.

The process of the present invention provides at least two significant advantages. First, the primary and secondary oxidations defined by steps (1)–(7) provides a terephthalic acid product which contains a total concentration of 4-carboxybenzaldehyde and p-toluic acid of less than about 900 ppmw. This reduced concentration of impurities provides for a more efficient hydrogenation which may permit a reduction in the size of the hydrogenation apparatus and/or the contact time of the feed solution within the hydrogenation zone. Second, since the total concentration of 4-carboxyaldehyde and p-toluic acid fed to the hydrogenation reactor is less than about 900 ppmw, there is less (as compared to known purification processes) p-toluic acid in the hydrogenation product solution. As a result, the number and or size of the crystallizers for the recovery of purified terephthalic acid may be reduced and the crystallization may be simplified. Also, the amount of material, i.e., water solvent containing dissolved impurities, that must be purged from the production system is reduced since the concentration of p-toluic acid had been reduced. Another advantage of our novel process is provided by step (10) wherein solvent is evaporated from at least one of the crystallizers constituting the crystallization zone and condensed and recycled to one of the subsequent crystallizer stages. The advantages provided by this step include the recovery of terephthalic acid in an improved crystalline form with less "fines", i.e., small crystals or particles of TPA, which can cause problems in the handling and conveying of the TPA. Another advantage is the product recovery at ambient or approximately ambient pressure.

BRIEF DESCRIPTION OF THE DRAWINGS

Accompanying

DETAILED DESCRIPTION

Figure 1:
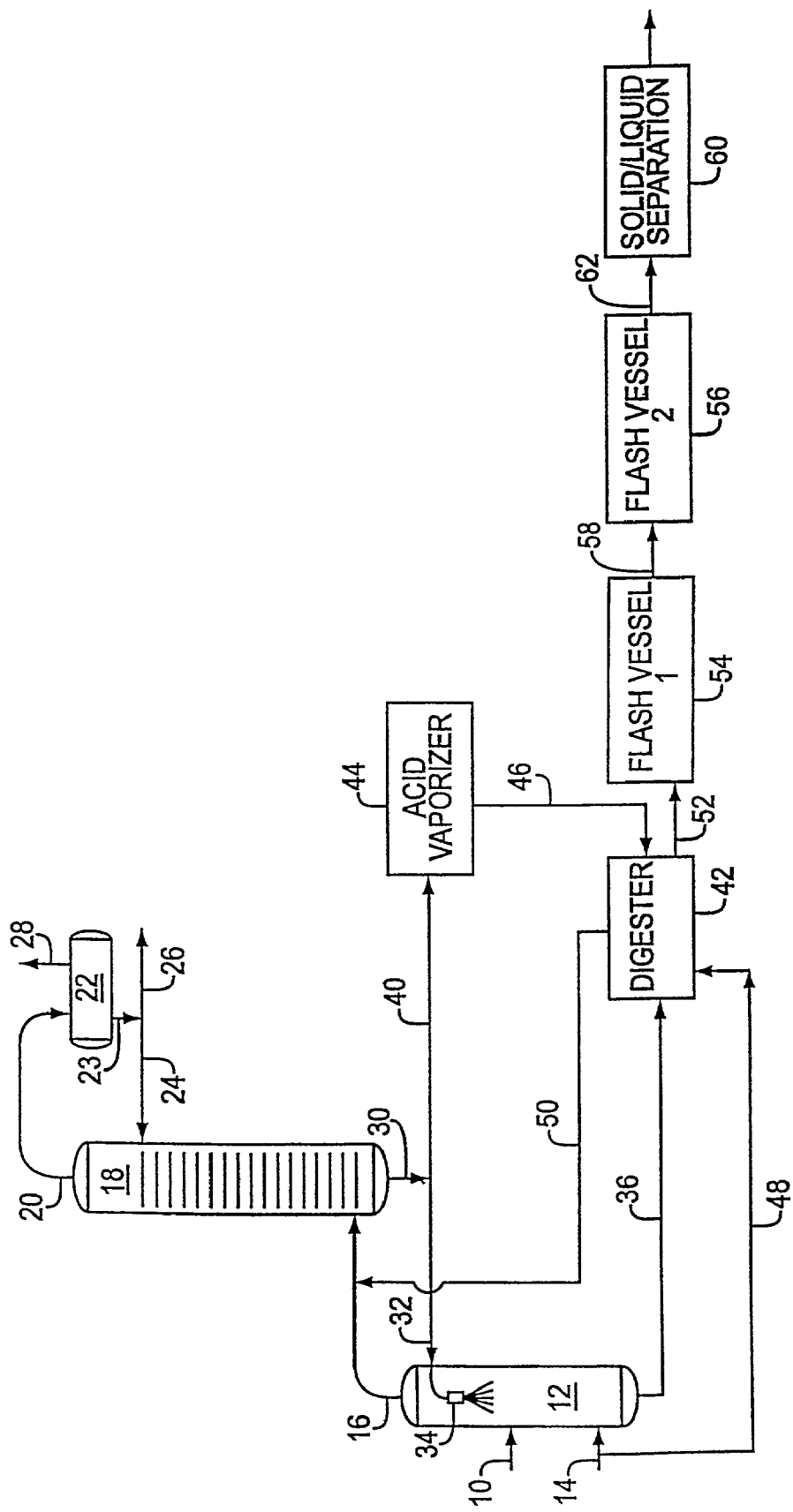
FIGS. 1 and 2 are process flow diagrams illustrating a system embodying the principles of the process of the present invention. While the present invention is susceptible to embodiment in various forms, there is shown in the accompanying FIGS. 1 and 2 and hereinafter described in detail a preferred embodiment of the invention. The present disclosure is to be considered as an exemplification of the invention without limitation to the specific embodiment illustrated, however.

Referring to accompanying FIG. 1, step (1) of our novel process may be carried out in a first oxidation zone comprising reactor vessel 12. A feed mixture comprising a dialkyl benzene compound such as p-xylene, aqueous acetic acid, and a suitable oxidation catalyst are fed to first oxidation reactor 12 via conduit 10. The acetic acid reaction medium or solvent feed typically contains up to about 15 weight percent water. If desired, the dialkyl benzene compound and/or acetic acid solvent containing catalyst components may be fed to reactor 12 at a plurality of points along the side of the reactor 12. A molecular oxygen-containing gas under pressure is continuously fed via conduit 14 to reactor 12 at or near the base of the columnar reaction vessel. The oxygen-containing gas, e.g., oxygen, oxygen-enriched air or, preferably, air, normally is fed at or near the base of the columnar reaction vessel. The flow rate of the oxygen-containing gas to reactor 12 is controlled to maintain between about 2 and 9, preferably about 2 to 5, volume percent oxygen (calculated on a dry, solvent free basis) in the off-gas which exits the reactor via conduit 16. The reactants in reactor 12 are maintained at an elevated pressure sufficient to maintain the contained, volatilizable reaction medium substantially in the liquid state at the reaction temperature. The temperature and pressure within reactor 12 are about 150 to 180° C. and about 3.5 to 13 bara (about 50 to 189 psia) preferably about 155 to 165° C. and about 5.2 to 6.9 bara (about 75 to 100 psia).

Reactor 12 typically is a columnar, pressurized, oxidation reactor vessel wherein liquid-phase exothermic oxidation of the dialkyl aromatic compound by the oxygen-containing gas takes place in the presence of the oxidation catalyst. The first oxidation zone may comprise a single reactor or a plurality of reactors arranged in parallel. The reaction medium contained in reactor 12 thus comprises the oxygen-containing gas, the dialkyl benzene compound that is to be oxidized to terephthalic acid product, the catalyst, and the aqueous, acetic acid solvent. The amount of water present normally does not exceed about 15 weight percent, preferably about 4 to 6 weight percent, based on the weight of the water and the acetic acid. Typically, the generally-cylindrical, first oxidation vessel has a height to diameter ratio in the range of about 3 to 20.

The catalyst systems that may be employed in the oxidation process include any catalyst system conventionally used for liquid-phase oxidation of an alkyl aromatic hydrocarbon. A suitable catalyst system comprises a mixture of cobalt, manganese and bromine compounds or complexes, soluble in aqueous acetic acid. The atomic ratio of the Co:Mn:Br combination of catalyst elements preferably is in the range of about 5 to 40:1.0:4 to 40, more preferably a Co:Mn:Br atomic ratio of about 16 to 40:1.0:16 to 40.

During the course of the oxidation reaction, exothermic heat of reaction generated by the oxidation of the dialkyl benzene compound, is removed from reactor 12 by vaporization of a portion of the liquid reaction medium. In accordance with step (2) of the present process, the vaporized liquid reaction medium (off-gas), along with the oxygen-depleted process gas containing a minor amount of decomposition products and bromine-containing compounds, pass upwardly through reactor 12 and are introduced via conduit 16 into a condenser system such as water column 18. The condensable components of the vapors collected in column 18 consist primarily of the acetic acid solvent that is returned to reactor 12 via conduits 30 and 32 and spray head 34.

As shown in FIG. 1, overhead aqueous vapors exit the upper portion of water removal column 18 through conduit 20 and fed to condenser 22. The composition of the condensable components of the aqueous vapors collected in condenser 22, known as the distillate, is greater than 98 weight percent water. A portion of the distillate is returned as reflux to the fractionating zone of column 18 via conduits 23 and 24. The remainder of the distillate is removed for disposal via conduits 23 and 26. The non-condensable components are vented via conduit 28 from the production system or may be transported to a pollution control device for further treatment, if desired.

A distilled bottoms liquid comprising partially dewatered acetic acid solvent, e.g., acetic acid containing about 4 to 12 weight percent water, exits the lower portion of the water removal column 18 via conduit 30. A portion of the partially de-watered solvent is recycled directly to the reactor 12 via conduit 32. This amount ranges from about 10 to 100 percent. The partially de-watered solvent is fed to the reactor 12 by one or more spray nozzles 34, which may be located below exit conduit 16 and above the phase separation of the gas/liquid contents of the reactor 12. Another portion of the partially de-watered solvent may be removed via conduit 40. Some or all of the condensed acetic acid may be returned to reactor 12 via feed stream 10.

In operation, first pressurized oxidation reactor 12 produces terephthalic acid product that is sparingly soluble in the aqueous process solvent and is removed through a lower exit port located at or near the base of the reactor as a slurry in the solvent which also contains dissolved catalyst components. The oxidation process in reactor 12 also produces by-products such as mono-carboxylic acids such as 4-carboxybenzaldehyde and p-toluic acid. At least a portion of these mono-carboxylic acids are solids which may be contained within the crystals of the terephthalic acid. Typically, these mono-carboxylic acids are present in concentration of about 900 ppmw 4-carboxybenzaldehyde and p-toluic acid. These mono-functional compounds are undesirable by-products since they function as polymer chain terminators and thus can result in the formation of low molecular weight polyesters such as poly(ethylene terephthalate) produced from terephthalic acid and ethylene glycol.

In accordance with steps (3) and (4) of our novel process, the slurry of terephthalic acid product and mono-carboxylic acid by-products is continuously withdrawn as a slurry in the aqueous, acetic acid process solvent, which also contains dissolved catalyst, from the bottom portion of reactor 12 and conveyed via conduit 36 to a second pressurized oxidation zone shown in FIG. 1 as reactor 42. The second oxidation zone may be a single, agitated reactor as depicted in FIG. 1 or two or more agitated reactors may be arranged in series or parallel. The aqueous acetic acid solvent typically contains about 5 to 12 weight percent water, based on the weight of the water and the aliphatic, carboxylic acid. A molecular oxygen-containing gas also is fed by means of conduit 48 to second oxidation reactor 42 wherein the 4-carboxybenzaldehyde and p-toluic acid by-products are further oxidized to the desired terephthalic acid. As in the case of the feed to the first oxidation reactor, the oxygen-containing gas may be oxygen, oxygen-enriched air or, preferably, air. The oxygen-containing gas normally is fed at or near the base of second oxidation reactor 42 below the surface of the liquid contents of the reactor.

The flow rate of the oxygen-containing gas to reactor 42 may be controlled to maintain between 0 and about 5, preferably about 0 to 1, volume percent oxygen (calculated on a dry, solvent free basis) in the off-gas which exits the reactor via conduit 50. The flow rate of oxygen-containing gas to reactor 42 normally is from 0.001 to 3 volume percent, preferably 0.001 to 2 volume percent, of the flow rate of oxygen-containing gas to reactor 12. The small amount of air fed to the second oxidation reactor 42 limits the oxidative decomposition of the acetic acid solvent, yet facilitates the conversion of the by-product mono-carboxylic acids to terephthalic acid.

The first oxidizer reactor described above accomplishes substantially all of the oxidation while operating at moderate pressure and temperature. The primary obstacle in achieving sufficient conversion of the dialkyl benzene compound to terephthalic acid in the primary oxidizer system is mass transfer limitations associated with oxygen diffusion to the partially oxidized products embedded or contained in the terephthalic acid, i.e., the partially oxidized, mono-carboxylic acid by-products may be encased within terephthalic acid crystals. Therefore, it is relatively easy to oxidize most of the dialkyl benzene compound to terephthalic acid even under moderate conditions. However, to achieve sufficiently complete conversion requires overcoming these mass transfer limitations. Operation of the first oxidation zone under moderate conditions of pressure and temperature can aid in the formation of small or fine crystals that can be dissolved and recrystallized in the second oxidation zone. When the small or fine crystals are dissolved in the second oxidation zone, the co-crystallized by-products are accessible for further oxidation.

The materials in second oxidation reactor 42 are maintained at an elevated pressure sufficient to maintain the contained, volatile reaction medium substantially in the liquid state at the reaction temperature. The temperature and pressure within reactor 12 are about 185 to 230° C. and about 4.5 to 18.3 bara (about 65 to 265 psia), preferably about 205 to 215° C. and about 13.4 to 17.2 bara (about 195 to 250 psia). The heat required for the operation of the second oxidation zone may be provided by supplying a vapor phase solvent to the second oxidation reactor and allowing the vapor phase solvent to condense. The vapor phase solvent normally will be at a pressure sufficient to allow the vapor to pass into the second oxidation reactor and to provide sufficient heat to the contents of the second oxidation reactor. For example, partially de-watered acetic acid may be fed from water removal column 18 to acid vaporizer 44 via conduits 30 and 40. The acid vaporizer 44 brings the partially de-watered acetic acid to a temperature and pressure sufficient to maintain the desired temperature within the second oxidation reactor 42. The design of the acetic acid vaporizer normally requires the availability of a heat transfer fluid such as Dowtherm or high pressure steam that can be used to vaporize the acetic acid. The acetic acid vapor is transferred from the acid vaporizer 44 to second oxidation reactor 42 via conduit 46.

An off-gas stream comprising vaporized liquid reaction medium along with the oxygen-depleted process gas containing a minor amount of decomposition products and bromine-containing compounds is removed from the upper section or top of second oxidation reactor 42 and fed via conduits 50 and 16 to a condenser system such as water column 18. The condensable components of the off-gas stream consisting primarily of acetic acid solvent that may be recovered as described above.

The terephthalic acid product is removed from second oxidation reactor 42 as a slurry in the aqueous, acetic acid process solvent, which also contains dissolved catalyst components via conduit 52. The slurry removed from reactor 42 typically comprises from about 20 to 40 weight percent solids and contains less than a total of about 900 ppmw, based on the weight of the solids present, of incomplete oxidation products, primarily 4-carboxybenzaldehyde and p-toluic acid. The total concentration of 4-carboxybenzaldehyde plus p-toluic acid typically is in the range of about 400 to 900 ppmw.

The slurry product from the second oxidation reactor 42 (second oxidizer product) may be cooled before being introduced into a solid/liquid separation and, optionally, a solid drying system. Preferably, the slurry product from the second oxidation reactor 42 is fed to a flash evaporation zone wherein the temperature and pressure of the second oxidizer product are reduced by flash evaporation. The flash evaporation zone may comprise one or, preferably, a plurality of flash vessels wherein the slurry product is cooled by staged or sequential pressure reduction evaporation. As shown in FIG. 1, to cool the slurry, conduit 52 leads to a first flash vessel 54. From there, conduit 58 leads to a second flash vessel 56. The first and second flash vessels 54 and 56 provide for a staged pressure reduction from reactor 42. This staged or sequential pressure reduction serves two purposes. First, it eliminates the need for pumping between the units. Second, the adiabatic flash from the pressure reduction between reactor 42 and first flash vessel 54 allows for the first flash vessel 54 to act as an evaporative crystallizer. The average size of the crystals of terephthalic acid crystals may increase in the first flash vessel 54. Vapor from both flash vessels 54 and 56 may be routed to a condenser (not shown).

First flash vessel 54 may be operated at a temperature of about 170 to 190° C. and a pressure of about 2.4 to 5.2 bara (about 35 to 75 psia). The slurry stream from first flash vessel 54 is fed to second flash vessel 56, which is another adiabatic flash tank at temperatures from 60 to 100° C. and a pressure of 0.3 to 0.8 bara (about 5 to 12 psia). Although two flash vessels are shown in FIG. 1 for cooling and cyrstallization, either less than or more than two may be employed or another cooling method may be used.

The cooled slurry is conveyed via conduit 62 to solid/liquid separation zone 60 wherein the solid terephthalic acid is separated from the aqueous acetic acid solvent/reaction medium using conventional liquid/solid separation means. After separation, the cake of the terephthalic acid is washed, for example, with cooled acetic acid from the water removal column 18. The wet filter cake may be dried to evaporate the residual acetic acid from the cake. A dried product is obtained from the solid/liquid separation device 60. The composition of this product is essentially the same as the composition of the solids present in the slurry product from second reaction zone 42.

Figure 2:
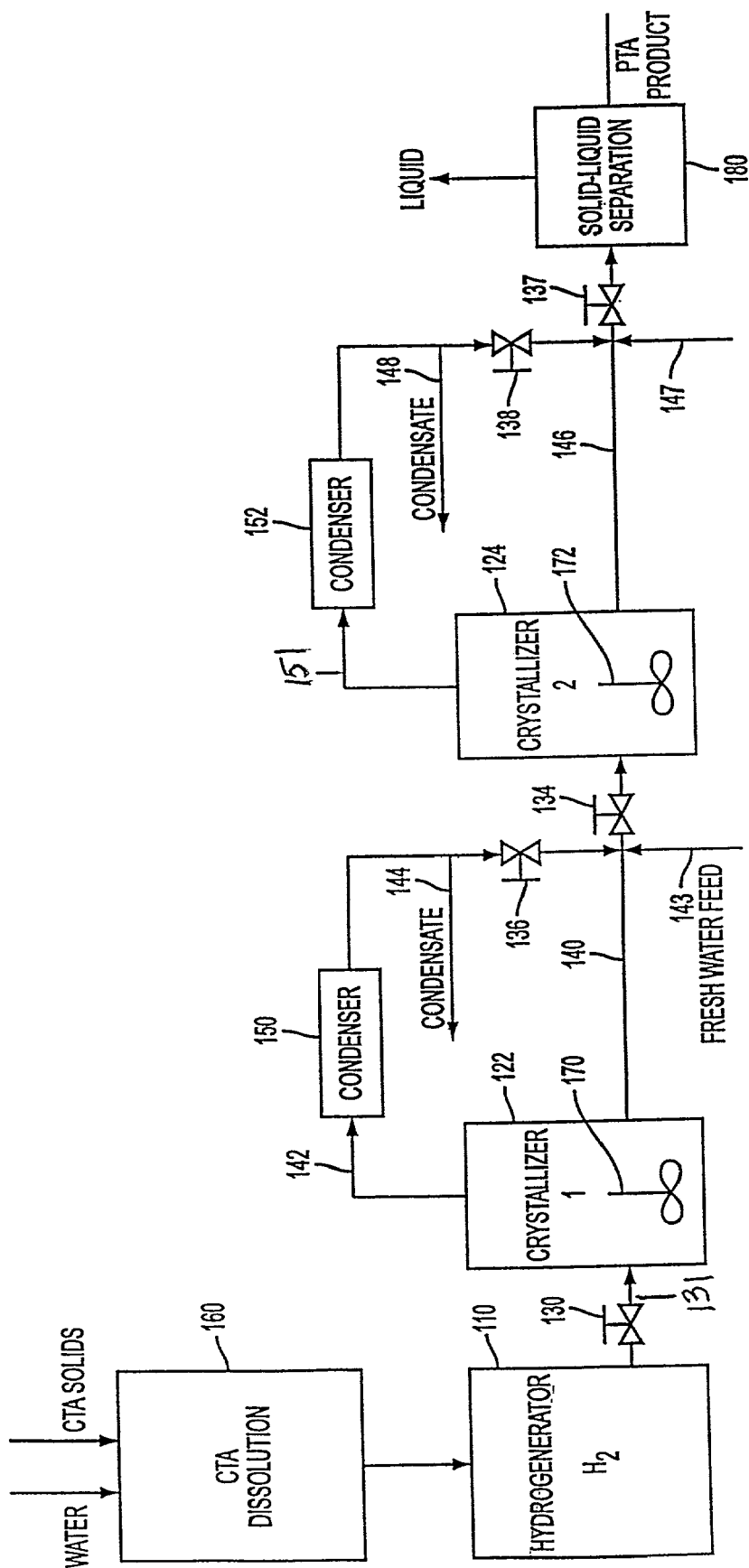

The purification of the second oxidizer product in accordance with step (6) of the present process comprises hydrogenating the second oxidizer product to convert 4-carboxybenzaldehyde to p-toluic acid and the color bodies, or precursors of color bodies, to colorless compounds. Referring to FIG. 2, water and the second oxidizer product (CTA) are fed to CTA Dissolution vessel 160. The solution typically comprises about 10 to 35 weight percent terephthalic acid solids in solvent water, preferably about 25 to 35 weight percent terephthalic acid, in solvent water. The terephthalic acid solution is formed by heating the solvent or slurry of terephthalic acid to a temperature that is sufficient to dissolve the terephthalic acid at the concentration desired, e.g., temperatures in the range of about 260 to 320° C. Solution temperatures in the range of about 260 to 320° C. using a solvent such as water require that the solution be maintained at an elevated pressure, e.g., a pressure in the range of about 46.9 to 113 bars absolute—bara (680–1640 pounds per square inch absolute (psia).

The terephthalic acid solution is fed to hydrogenation reactor 110 wherein the solution is subjected to liquid phase hydrogenation by contacting the liquid solution with hydrogen in the presence of a hydrogenation catalyst, e.g., a noble Group VIII metal on a catalyst support material, to cause certain of the impurities to be hydrogenated to other compounds. For example, fluorenones and 4-CBA are converted to fluorenes and p-toluic acid, respectively. Assuming that there is substantially complete conversion of 4-CBA to p-toluic acid and assuming that the terephthalic acid solution fed to the hydrogenation reactor has a combined total concentration of 4-CBA and p-toluic acid of less than about 900 ppmw, e.g., about 400 to 900 ppmw, then the concentration of p-toluic acid alone in the product stream from the hydrogenation reactor 110 is less than about 900 ppmw, based on the terephthalic acid present.

The temperature of the hydrogenation product stream typically is in the range of about 260 to 320° C. The hydrogenation product stream is fed through valve 130 and conduit 131 to a crystallization zone comprising a plurality or sequence of series-connected crystallizer stages that together operate to reduce the temperature of the post-hydrogenation stream to a lower temperature, typically about 75 to 150° C., more typically about 90 to 110° C. The reduction in temperature is accompanied by a concurrent precipitation of terephthalic acid from solution in the form of a white crystalline solid. The crystalline terephthalic acid in the final stage of crystallization is separated from the solvent using conventional a solid-liquid separation device such as a centrifuge or rotary vacuum filter. The crystallization zone may comprise two to eight, preferably three to six, most preferably four or five, crystallizers or crystallizer stages, The numbers of crystallizer stages employed in the process may affect the quality of the final product. The correct staging of the temperatures of the sequence of series-connected crystallizer stages will increase the purity of the final product with respect to p-toluic acid.

The plurality of crystallizer stages includes a first and a last crystallizer stage. The temperature within the first crystallizer stage normally is in the range of about 200 to 260° C. and the temperature within the last crystallizer stage normally is in the range of about 80 to 100° C. The operating temperatures of the crystallizer stages may become successively lower from the first to the last crystallizer stage. The last crystallizer stage produces a purified terephthalic acid slurry, which contains on a solid basis less than 150 ppmw p-toluic acid. In accordance with the present invention, terephthalic acid is crystallized in a first crystallizer stage by cooling the hydrogenation feed stream by controlled rate evaporative cooling (or flashing) by a reduction of the pressure (as compared to the feed stream pressure) within the first crystallizer or crystallizer stage. Solvent removed as a vapor from the crystallizer is condensed and some or all of the condensed solvent is returned to the crystallization zone at a point downstream from the crystallizer from which the solvent vapor was removed. Additional aromatic dicarboxylic acid is crystallized in a second crystallizer stage at a second temperature, less than the first temperature, while allowing solvent evaporation. Solvent, either condensed from solvent vapor produced in the preceding crystallizer and/or fresh solvent, may be added to the second crystallizer stage.

Each of the plurality of crystallizer stages has a mass flow rate of material entering and exiting the crystallizer stage. The mass flow rate of material entering the first crystallizer stage may equal 0.7 to 1.3 times the mass flow rate of material exiting the last crystallizer stage. Preferably, the mass flow rate of material entering the first crystallizer stage is substantially equal to the mass flow rate of material exiting the last crystallizer stage.

Each crystallizer stage of the process of our invention has a plurality of operational similarities comprising the following main elements:
1. A crystallization unit or vessel (crystallizer) equipped with an agitation means such as one or more impellers;
2. A feed line to the crystallizer;
3. A product removal line from the crystallizer;
4. A solvent distillate or vapor removal line from the crystallizer leading to a condenser wherein some or all of the solvent vapor is condensed; and
5. A solvent feed line to a downstream point or portion of the crystallzation zone for feeding the liquid condensed in the condenser.

The crystallization unit is a well-mixed vessel containing a slurry of terephthalic acid crystals. The solvent typically is water saturated with terephthalic acid at the operating temperature of the crystallizer. The operating temperature of each crystallization unit in combination with the temperature and concentration of the feed stream determines how much terephthalic acid will crystallize in each stage. To crystallize a larger portion of the terephthalic acid, the temperature must be lowered to a point where the solubility of terephthalic acid in the water solvent is reduced to allow more terephthalic acid to crystallize. Independent control of the pressure determines the operating temperature of the crystallization units. Pressure control can be accomplished by regulating the back-pressure in the crystallization units using, for example, but not limited to a valve in the vapor line.

As a result of reduced pressure (relative to the pressure of the feed stream to the crystallization unit), solvent evaporates and is removed from the crystallization unit as a vapor, thus concentrating the solution. A portion of the terephthalic acid precipitate crystallizes on crystals already existing in the vessel, and a portion of the terephthalic acid nucleates as separate new crystals. The amount of terephthalic acid that is transferred from the liquid phase to the solid phase is a function of the operating temperature (controlled by pressure reduction) of the crystallizer and the TPA equilibrium saturation concentration at that temperature.

Normally, the feed to the first crystallizer is fed below the surface of the slurry contained therein toward the bottom of the vessel where the hydrostatic head is highest. The increased pressure at this point in the crystallization unit and the surrounding liquid prevent excessive flashing. Agitation devices such as impellers are provided in the crystallization units. When the hydrogenation reactor product stream is introduced to the first crystallization unit at a zone of sufficient mixing, local high super-saturation, which promotes the formation of small (or fine) crystals, can be minimized.

A product stream is continuously withdrawn from each crystallization unit. The product stream preferably is removed from a well-mixed zone of the crystallization unit such that the contents of the product stream represent an average of the overall contents within each crystallization unit. The product stream is fed to a successive or subsequent crystallizer stage operated at a lower temperature, preferably to a well-mixed zone of the next crystallization unit. Because each successive crystallization unit operates at a lower temperature, a portion of the terephthalic acid remaining in solution crystallizes, which portion is determined by the equilibrium terephthalic acid concentration at the operating temperature of the second crystallization unit 124.

As mentioned above, solvent distillate or vapor is continuously removed from the first and subsequent crystallizer stages and transported to a condenser to cool and condense the vapor. Either a portion or all of the vapor may be condensed at this point. In addition, a sub-cooling of the vapor to a temperature substantially below the boiling point can also be accomplished within the condenser. All or a portion of the condensed solvent is recycled to the crystallization zone at a point downstream from the crystallizer from which the solvent was removed as a vapor. Preferably, the condensed solvent is recycled to the crystallization zone by feeding the condensed solvent to the product removal line of the crystallizer from which the solvent was removed as a vapor. Any condensed solvent not returned or recycled to the crystallization zone may be utilized elsewhere in the terephthalic acid purification system, e.g., in preparing the aqueous solution feed to the hydrogenation reactor. The final crystallization unit acts as a hold-up vessel for the slurry, retaining the slurry before a solid-liquid separation step. The second and subsequent crystallizers operate in a manner similar to that of the first crystallizer stage.

Condensed solvent from an upstream crystallizer stage may be recycled to an immediately downstream crystallizer stage or recycled to a crystallizer stage other than an immediately downstream crystallizer stage. Both condensed solvent and fresh solvent may be supplied to one of the subsequent crystallizer stages.

The product stream from any or all of the crystallizer stages may be diluted using a dilution liquid such as water at a temperature which is the same as, or substantially the same as, the operating temperature of the crystallizer stage from which the product stream was removed. The addition of the dilution liquid to the product stream has the effect of reducing the overall concentration of terephthalic acid and any impurities present in the product stream. If no dilution liquid is added to the product stream from each crystallizer, the overall concentration of terephthalic acid in each product stream continues to rise. In crystallization processes in which dilution liquid is not recycled, the product stream from the hydrogenation reactor is thus at such a dilution that the process will yield a pre-determined solid terephthalic acid concentration after the final crystallizer stage. That is, by knowing the amount of liquid added and removed and by knowing the amount of terephthalic acid crystallizing, the solid TPA concentration can be determined. By the addition of dilution water to the product stream from each crystallizer stage, the dilution required in the initial feed stream is much lower.

The dilution liquid added to the product stream can originate from a number of sources. Firstly, the condensate from the crystallizer stage from which the product is withdrawn may be condensed and partially or wholly recycled back to the product stream from that stage. Secondly, a fresh solvent, e.g., water, supply can be used, in an amount that is greater than, less than or equal to the amount of liquid removed in the form of distillate. Thirdly, if more than one crystallizer stage is being used, condensate from a stage other than the immediately preceding stage may be recycled to the crystallizer stage of interest. This condensate normally is heated to the same temperature as the operating temperature of the preceding crystallizer stage.

In each case, either a portion or all of the condensed solvent is recycled to the product feed supplying the crystallizer stages or additional solvent is supplied to the crystallizer stages or a combination of the two may be used. If more than two crystallizer stages are provided, the percentage of solvent supplied to each crystallizer stage may be varied. For example, some crystallizer stages may be supplied with an amount of solvent equal to the amount evaporated in the preceding stage, and some of the crystallizer stages may be supplied with no solvent.

The addition point for the dilution water back into the system may be at some point in the transfer line between crystallizers. This line normally contains a valve to control the flow rate of product from one crystallizer stage to the next. The residence time for a crystallizer stage is given by the volume of the crystallizer stage divided by the product slurry volumetric flow rate from the crystallizer stage. As an alternative to transfer line/feed line addition, the dilution liquid may be added directly to the crystallization unit. In this case, the dilution water preferably is added below the surface of the liquid, most preferably at the base of the crystallization unit, in a well mixed zone.

When all of the distillate from each crystallization unit is recycled to the product stream from that crystallization unit, the terephthalic acid concentration entering the crystallizer stages will be equal to each other irrespective of whether the TPA is in the liquid phase or the solid phase. Thus, the original feed stream liquid TPA concentration will be approximately equivalent to the final product solids hold-up concentration given that only a minor portion of terephthalic acid will remain in solution and not crystallize.

Compared to sequential terephthalic acid crystallization processes wherein there is no downstream recycle of condensed solvent, the stream from the hydrogenation reactor to the first crystallization unit may be more concentrated and have a reduced flow rate. Likewise, a reduction of feed flow rates from one crystallizer stage to the next results in a reduction in product flow rates. To maintain a pre-defined residence time with reduced feed flow rates, the volume of the crystallization units must be reduced. With a substantially constant flow rate, for example, the upstream, higher temperature and downstream, lower temperature crystallizer stages can have a substantially equal volume yet still have the same residence time.

In general, the strategy for selecting the temperature profile for a number of crystallizer stages has been to select the temperatures which crystallize smaller portions of terephthalic acid in each stage than the stage before. It has been established that this technique will not only crystallize less terephthalic acid in each downstream stage but it will also minimize contamination of the product by p-toluic acid. The ideal case where this mechanism would be taken greatest advantage of is in a series of infinite crystallizer stages, approximating batchwise conditions. The limit of practical operation does not allow for this. In the current invention, the higher terephthalic acid concentration in the original feed stream enhances this mechanism, as higher terephthalic acid concentrations cause more of the terephthalic acid to crystalize at higher temperatures (in the upstream stages).

The product removal line from the final crystallizer feeds a conventional solid-liquid separation apparatus for the recovery of the crystalline terephthalic acid product containing less than about 150 ppmw p-toluic acid. Since the temperature of the last crystallizer stage may be less than the normal boiling point for the solvent, a vacuum filter (instead of a pressure filter) may be used. The wet crystalline terephthalic acid may be washed before being discharged to a dryer. The filtered mother liquor and the fluid used for washing are collected for recycle to the hydrogenation step. A portion of the filtrate liquid may be purged to reduce the build-up of impurities in the system.

Again referring to FIG. 2, the hydrogenation product is removed from hydrogenation reactor 110 and fed via valve 130 to first crystallization unit 122 at a point below the surface of the slurry contained in vessel 122, near the bottom of vessel 122, where the hydrostatic head is higher. An agitation device such as impeller 170 is provided in first crystallization unit 122 and other crystallization units as well. A product stream is continuously removed from first crystallization unit 122 via conduit 140. The product stream is removed from a well-mixed zone of the crystallization unit 122 such that the contents of the product stream represent an average of the overall contents within that crystallization unit 122. The product stream is fed via a valve 134 to a second, successive crystallizer vessel 124 that is operated at a pressure and temperature lower than the pressure and temperature within crystallizer 122. The product stream is fed to a well-mixed zone of crystallization unit 124. Because the successive crystallization unit 124 operates at a lower temperature, a portion of the TPA remaining in solution crystallizes, which portion is determined by the equilibrium TPA concentration at the operating temperature of the second crystallization unit 124.

Solvent vapor is removed continuously from first crystallizer stage 122 via conduit 142 and fed to heat exchanger 150 wherein all or a portion of the solvent is condensed. Sub-cooling of the vapor to a temperature significantly below the boiling point also can be accomplished with the heat exchanger. A portion or all of the condensed solvent is fed to product stream 140 through a valve 136. Any condensed solvent not recycled to the product stream may be removed through conduit 144. Second crystallizer stage vessel 124 operates in a manner similar to that of first crystallizer stage 110 and includes crystallization unit 124 having impeller 172 therein. Product is removed from crystallization unit 124 via conduit 146. Solvent vapor is removed from second crystallization unit 124 and sent to condenser 152 wherein solvent vapor is condensed and the condensed solvent is recycled via valve 138 and/or eliminated via conduit 148. Fresh, additional solvent, e.g., water, may be added to the sequential crystallization system depicted in FIG. 1 via line 143 and/or line 147.

The crystallization product is removed from crystallizer 124 via conduit 146 and transferred via valve 137 to solid-liquid separation zone 180. The temperature at the last crystallizer stage may be less than the normal boiling point for the solvent which permits solid-liquid separation to be a vacuum filter. The solid-liquid separation 180 removes mother liquor from a crystalline cake in a first zone. The crystalline cake then is washed in the second zone.

Benefits and advantages provided by the process provided by the present invention include:
1. The same recovery of terephthalic acid per stage may be obtained as in the related art while staging crystallizer stage temperatures much closer to each other at the higher temperatures. This mode of operation may minimize shock cooling of the post-hydrogenation stream within the temperature range where most of the terephthalic acid is crystallized from solution. The use of conventional crystallization temperatures with the more pure crude aromatic dicarboxylic acid results in the crystallization of more of the aromatic dicarboxylic acid will crystallize from solution at the conventional temperatures.
2. For a given residence time and production rate, the volume of the upstream, higher temperature, higher pressure crystallizers may be much smaller than the volume required according to known processes since the initial terephthalic acid concentration in solution may be much higher while still targeting the same suspended solids content in the final product stream. Smaller crystallizer volumes result in a significant cost savings.
3. The ability to separate aromatic dicarboxylic acid crystals from mother liquor at temperatures below the boiling point of the solvent removes the necessity to use pressurized and enclosed filtration equipment to effect the separation. This permits the use of more cost effective solid-liquid separation devices while maintaining an effective separation.

EXAMPLES

The novel process of the present invention is further illustrated by the following examples. In the examples, parts given are by weight and percentages are by weight unless otherwise specified.

Example 1

This example demonstrates the ability to purify crude terephthalic acid having a p-toluic acid concentration of 429 ppmw to below the acceptable purity limit for purified terephthalic acid (150 ppm). It also demonstrates that this specification can be met by isolating the terephthalic acid at a temperature below the boiling point of the solvent.

A high-pressure autoclave was charged with the amounts of water (the solvent) and crude terephthalic acid listed in Table 1 for Experiments 1, 2 and 3. These amounts represent an approximate solution of 30% terephthalic acid in water. The p-toluic acid content in the crude terephthalic acid was 429.37 ppmw on a solids basis. The autoclave charges were heated to 280° C. and held at this temperature for one hour to ensure that all of the solids dissolved. To simulate a plurality of series-connected crystallizers, the autoclave charges were cooled to room temperature at a rate of 30° C. per hour. The autoclave charges were then reheated to 60° C., at which temperature the charges were held for one hour. The autoclave then was opened and solid-liquid separation was performed on the resulting slurries at 60° C. After cooling to 60° C., the p-toluic acid concentrations of the resulting purified terephthalic acid solids are shown in Table I.

TABLE I

| Material | Exper 1 | Exper 2 | Exper 3 |
| --- | --- | --- | --- |
| Crude terephthalic acid (parts) | 37.5015 | 37.505 | 37.4948 |
| Water (parts) | 87.7337 | 87.5131 | 87.4698 |
| p-Toluic acid (ppmw) | 429.37 | 429.37 | 429.37 |
| p-Toluic acid (ppmw) present in purified terephthalic acid (60° C.) | 155.71 | 91.66 | 79.12 |
| P-Toluic acid (ppmw) present in purified terephthalic acid (95° C.) | 113.03 | 64.96 | 36.81 |

In two of the three experiments, the purity of the resulting solids was well within the 150 ppm maximum p-toluic acid content for purified terephthalic acid. The terephthalic acid recovered in Experiment 1 had a p-toluic acid concentration of 155.71 ppmw.

Example 2

In this example demonstrating the effect of isolation temperature on the purity of the final product, portions of the room temperature autoclave charges resulting from Experiments 1, 2 and 3 of Example 1 were separately placed in a well-mixed vessel. Instead of reheating to 60° C. as was done for Example 1, the portions were reheated to 95° C. for Example 2, and were held at this temperature for 1 hour. Solid-liquid separation was performed at 95° C. to obtain samples of the solids, which were analyzed for p-toluic acid concentration. The results are also shown in Table I. As can be seen, isolating at the higher 95° C. temperature leads to a product with a lower p-toluic acid concentration than the material isolated at the lower 60° C. temperature. An increase in product purity can be achieved by raising the isolation temperature from 60° C. while still keeping the solid-liquid separation temperature below the boiling point of the solvent.

Example 3

A high-pressure autoclave was charged with the amounts of water and crude terephthalic acid listed in Table II for Experiments 4 and 5. These samples represent an approximate solution of 20% crude terephthalic acid in water solution. The concentration of p-toluic acid in the crude terephthalic acid solids was 429.37 ppmw. The samples were heated to 280° C. and held at this temperature for one hour to ensure that all of the solids dissolved. The samples were cooled to room temperature at a rate of 30° C. per hour. Then, as was done in the procedures of Examples 1 and 2, a portion of each sample was heat to 60° C. and separated at this temperature, and a portion of each sample was heated to 95° C. and separated at this temperature. The p-toluic acid concentrations of the resulting solids are shown in Table II.

TABLE II

| Material | Exper 4 | Exper 5 |
| --- | --- | --- |
| Crude terephthalic acid (parts) | 25.0104 | 25.0017 |
| Water (parts) | 99.9537 | 100.2292 |
| p-Toluic acid (ppmw) | 429.37 | 429.37 |
| p-Toluic acid (ppmw) present in purified terephthalic acid (60° C.) | 65.37 | 51.23 |
| p-Toluic acid (ppmw) present in purified terephthalic acid (95° C.) | 40.49 | 44.56 |

In Example 3, a more dilute solution was used than for Example 1 (20% vs. 30%). The crude terephthalic acid used for Example 1 and Example 2 had the same p-toluic acid concentration (429.37 ppm). Therefore, for Example 3, there was a lower p-toluic acid concentration in the initial diluted solution. Comparison of Table II with Table I demonstrates the benefit of having a lower p-toluic acid concentration in the initial solution on the final product purity.

Solid-liquid separation removes the solids from the mother liquor. Table III compares the mother liquor p-toluic acid concentrations for the experiments shown in Example 2 and Example 3 wherein the purified terephthalic acid was recovered at 95° C. When a lower concentration of crude p-toluic acid is used, there is less p-toluic acid in solution. This results in a lower p-toluic acid concentration in the mother liquor produced by solid-liquid separation. A mass balance shows that where there is a lower concentration of p-toluic acid in the mother liquor, the solids product also has a lower concentration of p-toluic acid.

The crude terephthalic acid used for Experiments 1–5 shown in Table III had a p-toluic acid concentration of 429.37 ppm. The amount of dilution was the parameter that was varied. However, by analogy, it can be presumed from Table III that if the purity of the crude starting material is increased while maintaining a constant level of dilution, then a more pure product will be produced.

TABLE III

| Material | Exper 1 | Exper 2 | Exper 3 | Exper 4 | Exper 5 |
| --- | --- | --- | --- | --- | --- |
| Crude terephthalic acid | 30% | 30% | 30% | 20% | 20% |
| Mother liquor p-toluic acid concentration (@95° C.) | 144.48 | 164.07 | 157.85 | 107.92 | 98.63 |

While the invention has been described in detail with respect to specific embodiments thereof, it will be appreciated that those skilled in the art, upon attaining an understanding of the foregoing may readily conceive of alterations to, variations of and equivalents to these embodiments. Accordingly, the scope of the present invention should be assessed as that of the appended claims and any equivalents thereto.

We claim:

1. Process for the production and recovery of a crystalline terephthalic acid composition containing less than about 150 parts per million by weight (ppmw) p-toluic acid, based on the weight of the crystalline terephthalic acid composition, by the steps comprising:
   (1) feeding (i) p-xylene, (ii) an aqueous acetic acid reaction medium having an oxidation catalyst comprising cobalt, manganese and bromine dissolved therein, and (iii) an oxygen-containing gas to a first pressurized oxidation reactor wherein liquid-phase, exothermic oxidation of the p-xylene occurs, wherein the temperature and pressure within the first pressurized oxidation reactor are maintained at about 150 to 180° C. and about 3.5 to 13 bar absolute—bara (about 50 to 189 pounds per square inch—psia);
   (2) removing from the upper portion of the first pressurized oxidation reactor a vapor comprising vaporized aqueous, acetic acid reaction medium and oxygen-depleted gas;
   (3) removing from the lower portion of the first pressurized oxidation reactor an oxidizer composition comprising (i) solid and dissolved terephthalic acid and p-toluic acid and (ii) the aqueous, acetic acid reaction medium having the oxidation catalyst dissolved therein;
   (4) feeding (i) the oxidizer composition of step (3) and (ii) an oxygen-containing gas to a second pressurized oxidation reactor wherein liquid-phase, exothermic oxidation of the p-toluic acid occurs, wherein the temperature and pressure within the second pressurized oxidation reactor are maintained at about 185 to 230° C. and about 4.5 to 18.3 bara (about 65 to 265 psia);
   (5) removing from the upper portion of the second pressurized oxidation reactor a vapor mixture comprising vaporized aqueous, acetic acid reaction medium and oxygen-depleted gas;
   (6) removing from the lower portion of the second pressurized oxidation reactor a second oxidizer composition comprising (i) solid and dissolved terephthalic acid and (ii) the aqueous, acetic acid reaction medium having the oxidation catalyst dissolved therein;
   (7) separating terephthalic acid from the (ii) the aqueous, acetic acid reaction medium of step (6) to obtain a terephthalic acid composition containing less than about 900 ppmw 4-carboxybenzaldehyde and p-toluic acid;
   (8) dissolving the terephthalic acid composition obtained in step (7) in water to form a solution containing about 10 to 35 weight percent dissolved terephthalic acid having dissolved therein less than about 900 ppmw 4-carboxybenzaldehyde and p-toluic acid, based on the weight of the terephthalic acid present, at a temperature of about 260 to 320° C. and a pressure sufficient to maintain the solution in the liquid phase and contacting the solution with hydrogen in the presence of a noble Group VIII metal hydrogenation catalyst to produce a hydrogenation product solution;
   (9) feeding the solution of step (8) to a crystallization zone comprising a plurality of series-connected crystallizers wherein the solution is subjected to rate-controlled evaporative cooling by sequential reduction in pressure and temperature to cause crystallization of terephthalic acid, wherein the pressure of the solution at the end of the crystallization zone is about ambient pressure or less;
   (10) condensing solvent evaporated from the crystallizers and returning the condensed solvent to the crystallization zone at a point subsequent to the crystallizer from which it was obtained; and
   (11) recovering said crystalline terephthalic acid composition containing less than about 150 parts ppmw p-toluic acid, based on the weight of the crystalline terephthalic acid composition, by solid-liquid separation at ambient pressure.

2. Process according to claim 1 wherein steps (1)–(7) comprise:
   (1) feeding (i) p-xylene, (ii) aqueous acetic acid reaction medium having oxidation catalyst components dissolved therein, and (iii) an oxygen-containing gas to a first pressurized oxidation zone wherein liquid-phase, exothermic oxidation of p-xylene occurs, wherein the temperature and pressure within the first pressurized oxidation reactor are maintained at about 150 to 180° C. and about 3.5 to 13 bar absolute (bara);

(2) removing from the upper portion of the first pressurized oxidation reactor a vapor comprising vaporized aqueous, acetic reaction medium and oxygen-depleted gas comprising carbon dioxide;

(3) removing from the lower portion of the first pressurized oxidation reactor an oxidizer composition comprising (i) solid and dissolved terephthalic acid and p-toluic acid and (ii) the aqueous, acetic acid reaction medium having the oxidation catalyst dissolved therein;

(4) feeding (i) the oxidizer composition of step (3) and (ii) an oxygen-containing gas to a second pressurized oxidation zone wherein liquid-phase, exothermic oxidation of the incomplete oxidation products occurs, wherein the temperature and pressure within the second pressurized oxidation reactor are maintained at about 185 to 230° C. and about 4.5 to 18.3 bara;

(5) removing from the upper portion of the second pressurized oxidation reactor a vapor comprising vaporized aqueous, acetic acid reaction medium and oxygen-depleted gas comprising carbon dioxide;

(6) removing from the lower portion of the second pressurized oxidation reactor a second oxidizer composition comprising (i) solid and dissolved terephthalic acid and (ii) the aqueous, acetic acid reaction medium having the oxidation catalyst dissolved therein; and (7) separating the terephthalic acid from the (ii) the aqueous, acetic acid reaction medium of step (6) to obtain the terephthalic acid composition containing less than about 900 ppmw 4-carboxybenzaldehyde and p-toluic acid.

3. Process according to claim 2 wherein step 1 is carried out at about 155 to 165° C. and about 5.2 to 6.9 bara in the presence of aqueous acetic acid reaction medium containing about 4 to 5 weight percent water having oxidation catalyst comprising cobalt, manganese and bromine dissolved therein; the second pressurized oxidation zone of step (4) is maintained at a temperature and pressure of about 205 to 215° C. and about 13.4 to 17.2 bara; and the terephthalic acid composition of step (7) contains about 400 to 900 ppmw 4-carboxybenzaldehyde and p-toluic acid.

4. Process according to claim 3 wherein the atomic ratio of Co:Mn:Br is about 5 to 40:1.0:4 to 40.

5. Process according to claim 1 wherein the second oxidizer composition of step (6) is fed to a flash evaporation zone wherein the temperature and pressure of the second oxidizer composition are reduced by flash evaporation.

6. Process according to claim 2 wherein the second oxidizer composition of step (6) is fed to a flash evaporation zone comprising (i) a first flash vessel operated at a temperature of about 170 to 190° C. and a pressure of about 2.4 to 5.2 bara and (ii) a second flash vessel operated at a temperature of about 60 to 100° C. and a pressure of about 0.3 to 0.8 bara, wherein the temperature and pressure of the second oxidizer composition are reduced by flash evaporation.

7. Process according to claim 1 wherein the solution of step (8) contains about 25 to 35 weight percent dissolved terephthalic acid; the hydrogenation product solution of step (8) has dissolved therein about 400 to 900 ppmw p-toluic acid, based on the weight of the terephthalic acid present, and the plurality of series-connected crystallizers consists of two to eight crystallizers.

8. Process according to claim 7 wherein the temperature of the first crystallizer is in the range of about 260 to 320° C. and the temperature of the last crystallizer is in the range of about 90 to 110° C. and the plurality of series-connected crystallizers consists of three to six crystallizers.

9. A process for the production of benzenedicarboxylic acid composition comprising:

(1) oxidizing a dialkyl benzene compound in the presence of an oxygen containing gas, an oxidation catalyst comprising a source of cobalt, manganese and bromine, and acetic acid solvent in a first pressurized oxidation reactor;

(2) removing an oxidation product mixture from the first pressurized oxidation reactor, said oxidation product mixture comprising a solid benzenedicarboxylic acid, p-toluic acid, and acetic acid solvent, and feeding said oxidation product mixture to a second pressurized oxidation reactor;

(3) further liquid phase oxidizing said oxidation product mixture in the second pressurized oxidation reactor while maintaining the temperature within said second pressurized oxidation reactor at about 185–230° C.; and (4) condensing within said second pressurized oxidation reactor a vapor phase solvent fed to said second pressurized oxidation reactor; and (5) removing from the second pressurized oxidation reactor a second oxidizer composition comprising (i) solid and dissolved benzenedicarboxylic acid and (ii) aqueous, acetic acid; and (6) separating benzenedicarboxylic acid from said aqueous, acetic acid of step (5); and (7) dissolving the benzenedicarboxylic acid obtained in step (6) in water to form a solution containing 10 to 35 weight percent dissolved benzenedicarboxylic acid at a temperature of 260 to 320° C. and a pressure sufficient to maintain the solution in the liquid phase and contacting the solution with hydrogen in the presence of a noble Group VIII metal hydrogenation catalyst to produce a hydrogenation product solution.

10. The process of claim 9, wherein at least part of the feed required for operating the second pressurized oxidation reactor at a temperature of about 185–230° C. is supplied by said vapor phase solvent.

11. The process of claim 9, wherein said vapor phase solvent is fed to said second pressurized oxidation reactor at a pressure sufficient to allow the vapor to pass into said second pressurized oxidation reactor and condense, while providing sufficient heat to the contents of the second pressurized oxidation reactor to maintain the temperature at about 185–230° C.

12. The process of claim 9, wherein the second oxidizer composition contains less than 150 ppmw p-toluic acid.

13. The process of claim 9, wherein said vapor phase solvent comprises acetic acid solvent.

14. The process of claim 9, wherein said vapor phase solvent comprises acetic acid solvent, and said oxidation product mixture comprises terephthalic acid and 4-carboxybenzaldehyde.

15. A process for the production of benzenedicarboxylic acid composition containing less than a total of about 150 ppmw carboxybenzaldehyde and toluic acid comprising:

(1) feeding (i) a dialkyl benzene compound, (ii) an aqueous acetic acid reaction medium having an oxidation catalyst comprising a source of cobalt, a source of manganese, and a source of bromine dissolved therein, and (iii) an oxygen-containing gas to a first pressurized oxidation reactor wherein liquid-phase, exothermic oxidation of the dialkyl benzene compound occurs, wherein the temperature and pressure within the first pressurized oxidation reactor are maintained at about 150 to 180° C. and about 3.5 to 13 bars absolute (bara);

(2) removing from the first pressurized oxidation reactor a vapor comprising vaporized aqueous, acetic reaction medium and oxygen-depleted gas;

(3) removing from the first pressurized oxidation reactor an oxidizer composition comprising (i) solid and dissolved benzenedicarboxylic acid and 4-carboxybenzaldehyde, and (ii) the aqueous, acetic acid reaction medium having the oxidation catalyst dissolved therein;

(4) feeding (i) the oxidizer composition of step (3), (ii) an oxygen-containing gas, and (iii) a vapor phase solvent to a second pressurized oxidation reactor wherein liquid-phase, exothermic oxidation of the incomplete oxidation occurs, wherein temperature and pressure within the second pressurized oxidation reactor are maintained at about 185–230° C. and about 4.5 to 18.3 bara, and condensing the vapor phase solvent within said second pressurized oxidation reactor;

(5) removing from the second pressurized oxidation reactor a second oxidizer composition comprising (i) solid and dissolved benzenedicarboxylic acid and (ii) aqueous, acetic acid; and (6) separating benzenedicarboxylic acid from said aqueous, acetic acid of step (5); and (7) dissolving the benzenedicarboxylic acid obtained in step (6) in water to form a solution containing 10 to 35 weight percent dissolved benzenedicarboxylic acid at a temperature of 260 to 320° C. and a pressure sufficient to maintain the solution in the liquid phase and contacting the solution with hydrogen in the presence of a noble Group VIII metal hydrogenation catalyst to produce a hydrogenation product solution;

(8) feeding the hydrogenation product solution to a crystallization zone to cause crystallization of benzenedicarboxylic acid; and (9) recovering solid, crystalline benzenedicarboxylic acid composition containing less than 900 parts ppmw 4-carboxybenzaldehyde and p-toluic acid.

16. The process of claim 15, wherein said benzenedicarboxylic acid composition comprises terephthalic acid, and said vapor solvent fed to the second pressurized oxidation reactor comprises an acetic acid solvent.

17. The process of claim 16, wherein said acetic acid solvent fed to the second pressurized oxidation reactor is partially de-watered acetic acid solvent.

18. The process of claim 15, wherein the vapor removed from the first pressurized oxidation reactor in step (2) is fed to a water removal column, a distilled partially de-watered acetic acid solvent is removed from the water removal column, and at least a portion of said de-watered acetic acid solvent is fed to said second pressurized oxidation reactor.

* * * * *